(12) United States Patent
Othman et al.

(10) Patent No.: US 9,051,541 B2
(45) Date of Patent: Jun. 9, 2015

(54) MRI-COMPATIBLE BIOREACTORS AND METHODS OF USING

(71) Applicant: NUtech Ventures, Lincoln, NE (US)

(72) Inventors: Shadi Othman, Lincoln, NE (US); Huihui Xu, Lincoln, NE (US); Karin Wartella, Lincoln, NE (US); Vahid Khalilzad-Sharghi, Lincoln, NE (US); Ian Bargar, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 13/953,984

(22) Filed: Jul. 30, 2013

(65) Prior Publication Data

US 2014/0030753 A1    Jan. 30, 2014

Related U.S. Application Data

(60) Provisional application No. 61/677,039, filed on Jul. 30, 2012.

(51) Int. Cl.
*C12M 1/34* (2006.01)
*G01N 24/08* (2006.01)

(52) U.S. Cl.
CPC ............. *C12M 41/46* (2013.01); *G01N 24/087* (2013.01); *C12M 1/34* (2013.01)

(58) Field of Classification Search
CPC ........ C12M 21/00; C12M 21/08; C12M 1/00; C12M 1/34; C12M 1/3407; C12M 23/00; C12M 23/22; C12M 23/06; A61K 6/00; A61K 35/00; A61K 35/12; A61K 35/32; A61B 1/00; A61B 5/00; A61B 5/05; A61B 5/053

See application file for complete search history.

(56) References Cited

U.S. PATENT DOCUMENTS

2011/0159590 A1* 6/2011 Shaaltiel ........................ 435/414
2011/0212500 A1* 9/2011 Boronyak et al. ............. 435/174
2014/0199679 A1* 7/2014 Panoskaltsis et al. ............. 435/2

OTHER PUBLICATIONS

Mahoney, C. Phase, Frequency, FOV. Datasheet [online]. Magnetic Resonance Imaging. Multiple data sources compiled by Mahoney. 1986-2009 [retrieved on Jul. 24, 2014]. Retrieved from the Internet: <URL:http://mri-info.net/welcome/?page_id=653>. specif. p. 2.*
Beutel, S. et al. 2011.In situ sensor techniques in modern bioprocess monitoring.Applied Microbiology and Biotechnology 21:1493-1505. specif. pp. 1493, 1496, 1498, 1500-1501.*
Klimant, I. 1997. Optical measurement of oxygen and temperature in microscale: strategies and biological applications. Sensors and Actuators B/ Chemical 38-39: 29-37. specif. pp. 29 and 36.*
Majors, P.D. 2008. NMR bioreactor development for live in-situ microbial functional analysis. Journal of Magnetic Resonance 192: 159-166. specif. pp. 159-161.*
Planchamp etal., "Hollow Fiber Bioreactor: New Development for the Study of Contrast Agent Transport Into Hepatocytes in Magnetic Resonance Imaging," *Biotechnol. Bioeng.*, 2004, 85:656-665.
Xu et al., "Magnetic resonance for monitoring osteogenesis in tissue-engineered construct in vitro," *Phys. Med. Biol.*, 2006, 51:719-732.

* cited by examiner

*Primary Examiner* — John S Brusca
*Assistant Examiner* — Sharon M Papciak
(74) *Attorney, Agent, or Firm* — Fish & Richardson P.C.

(57) ABSTRACT

This disclosure describes a MRI-compatible bioreactor that allows a biological sample to be imaged in culture without disrupting or compromising the culture.

18 Claims, 2 Drawing Sheets

MRI-COMPATIBLE BIOREACTORS AND METHODS OF USING

CROSS REFERENCE TO RELATED APPLICATIONS

This application claims the benefit of priority under 35 U.S.C. §119(e) to U.S. Application No. 61/677,039 filed Jul. 30, 2012. The prior application is incorporated herein by reference in its entirety.

TECHNICAL FIELD

This disclosure generally relates to bioreactors and, more specifically, MRI-compatible bioreactors, and methods of using such bioreactors.

BACKGROUND

Magnetic resonance imaging (MRI) can observe structural and functional changes associated with cell and tissue development, facilitating the use of MRI in translational research and clinical trials of tissue engineering. One problem when applying MRI to tissue engineering is that samples allocated in a test tube for imaging cannot be returned back to incubators and are, therefore, wasted due to potential contamination. In addition, samples removed from the incubator for imaging and, therefore, are not under consistent growth conditions or environments. Thus, there is a need for an approach that allows the functional outcome of cell or tissue constructs to be monitored non-invasively without interrupting or disturbing the culture.

SUMMARY

This disclosure describes a MRI-compatible bioreactor, which allows imaging of a growing biological sample without disrupting or disturbing the culture.

In one aspect, a MRI-compatible bioreactor system is provided. Such a system generally includes a bioreactor component that includes a tissue-imaging chamber and a support chamber. The tissue-imaging chamber and the support chamber generally are separated by a permeable support that allows for fluid communication between the chambers. At least the tissue-imaging chamber of the bioreactor component is configured to be received within a magnetic resonance (MR) imager and includes at least one fiber optic sensor and fluidics capable of fluidly communicating with a source of oxygen. The support chamber generally includes a heating element and fluidics capable of fluidly communicating with at least one reservoir, where the support chamber is configured to be able to comprise culture media and maintain the culture media under suitable conditions.

As described herein, the tissue imaging chamber is configured to fall within the field-of-view (FOV) of the MR imager, and the support chamber is configured to fall outside the FOV of the MR imager.

In some embodiments, the at least one fiber optic sensor is a temperature sensor. In some embodiments, the at least one fiber optic sensor is a CO2 sensor and/or a humidity sensor. In some embodiments, the support chamber further includes at least one non-fiber optic sensor. Representative non-fiber optic sensors include, for example, temperature sensors and/or pH sensors. In some embodiments, the at least one non-fiber optic sensor is in communication with a microcontroller.

In some embodiments, the MRI-compatible bioreactor system further includes a pump configured to promote fluid communication between the at least one reservoir and the culture media in the support chamber.

In some embodiments, a MRI-compatible bioreactor system further can include a microcontroller. A microcontroller can be in communication with the at least one fiber optic sensor, with the heater, or with the at least one fiber optic sensor and the heater, where the at least one fiber optic sensor is a temperature sensor.

In another aspect, a method of imaging a biological sample is provided. Such a method typically includes providing a MRI-compatible bioreactor system as described herein, where the tissue imaging chamber comprises a biological sample and the support chamber comprises culture media; inserting at least the tissue imaging chamber of the bioreactor component into a MR imager such that the tissue imaging chamber falls within the field-of-view (FOV) of the MR imager and the support chamber does not fall within the FOV of the MR imager; and imaging the biological sample using the MR imager.

The MRI-compatible bioreactor described herein can be inserted into the MR imager and imaged without disrupting the biological sample. In some embodiments, the methods include repeating the inserting and imaging steps at least twice, where repeating the inserting and the imaging steps at least twice does not require removing the biological sample or any portion thereof from the bioreactor and does not compromise the biological sample or the culture media. In some embodiments, the methods include repeating the imaging step at least twice, where the inserting step is performed only once.

In some embodiments, the methods also include exchanging the media in the support chamber with fresh media in the at least one reservoir via the fluidics. In some embodiments, the methods further include repeating the exchanging step at least twice separated by a period of time. Periods of time can be, for example, hours, days, weeks, or months.

As used herein, the biological sample refers to a tissue sample or a cell sample.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

The design of the MRI-compatible bioreactor described herein is highly innovative. With an MRI-compatible chamber designed for culturing cells and tissue, the bioreactor described herein is designed to integrate with a commercial MR imager, which can be used to assess the morphogenesis of developing tissue.

Conventional tissue culture bioreactors typically restrict the ability to apply non-invasive medical imaging modalities. Hollow fiber bioreactors (HFBRs) are the only MRI-compatible culture system (see, for example, Planchamp et al., 2004, *Biotechnol. Bioeng.*, 85:656-65). However, HFBRs are limited by their lack of consistent physiological conditions inside HFBRs due to, for example, their requirement for constant media perfusion. In addition, conditions within HFBRs are not detectable or easily regulated during MRI acquisition; for example, in HFBRs, temperature is measured outside the magnet, which is not a faithful representation of the cells' or tissues' direct surroundings.

Compared to existing methodologies, the MRI-compatible bioreactor described herein offers an integrated approach that takes full advantage of high-resolution MRI, currently, the most sophisticated clinically-viable imaging technique, by enabling dynamic assessment of developing constructs in a self-regulated and maintained culture environment.

Figure 1:
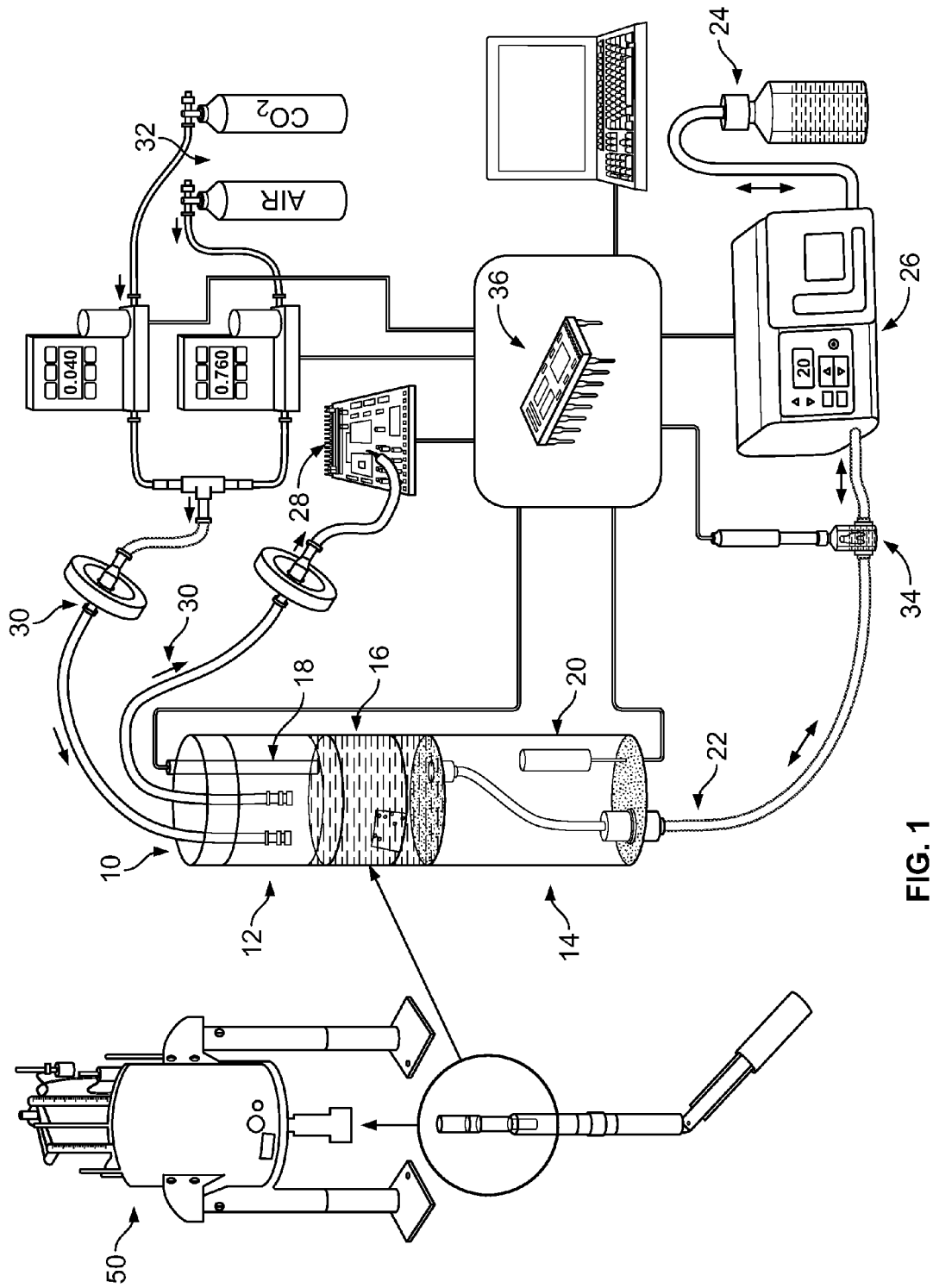
FIG. 1 shows a schematic of a representative MRI-compatible e-incubator.
Figure 2D:
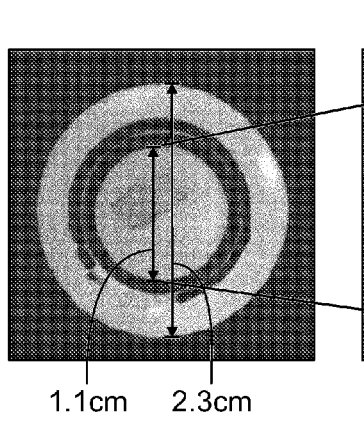
FIG. 2 shows the preliminary results of culturing osteogenic constructs in the e-incubator. Panel (a) shows an axial MRI of the chamber system, a 1.1 cm inner diameter tissue holder inside a 2.3 cm inner diameter TI chamber. Panel (b) and Panel (c) show axial MRIs at week-1 and week-2, respectively, acquired by a fast spin-echo sequence with the same acquisition parameters; the in-plane resolution was 97 micron square. The construct position was slightly different from week-1 to week-2 due to media exchange. Panel (d) is a graph showing the 12-hour time course of temperature (between 36 to 37° C.) and $CO_2$ (5%), where the sharp drops represent the event of media exchange every 6 hours.
Figure 2D:
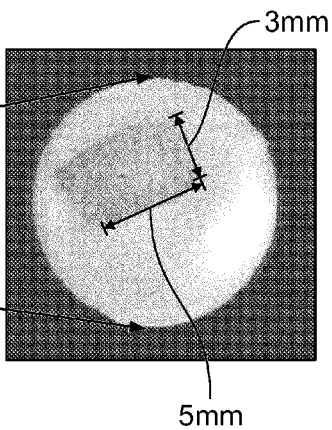
Figure 2D:
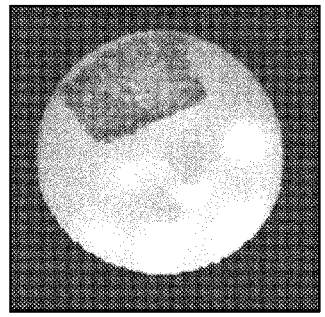
Figure 2D:
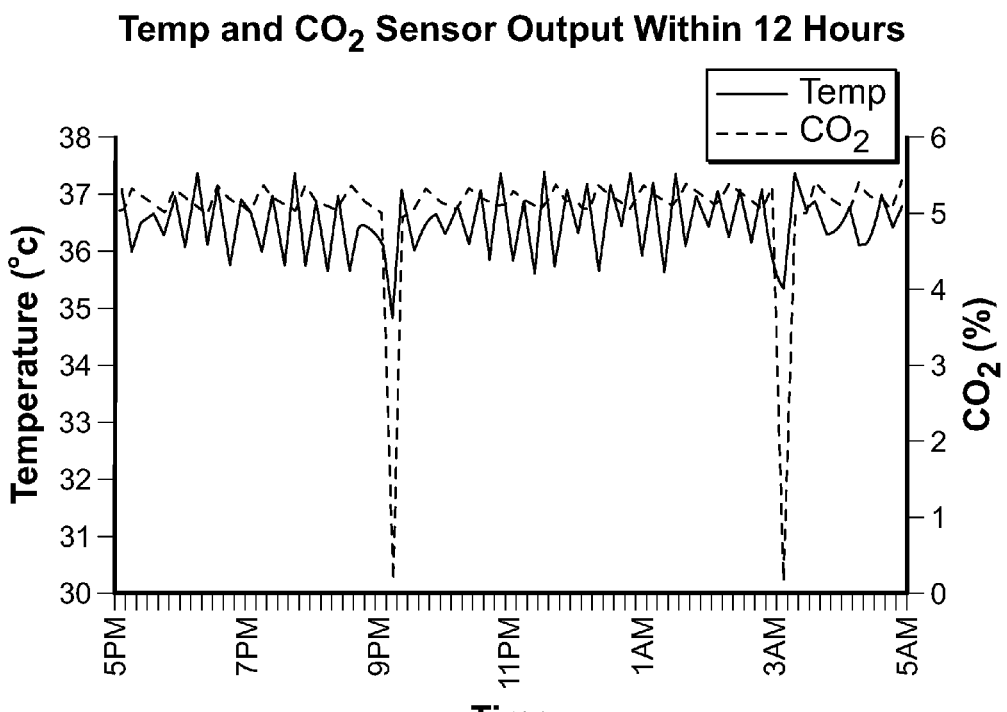

FIG. 1 shows one embodiment of a MRI-compatible bioreactor system 1 as described herein. An MRI-compatible bioreactor system 1 includes a bioreactor 10. As used herein, a bioreactor (or bioreactor component) 10 refers to a device that supports and maintains the viability of cells or tissues in culture and, in some instances, promotes the biological growth and/or development of the cells or tissues. In the embodiment shown in FIG. 1, the bioreactor component 10 is cylindrical, although any shape that a MR imager is capable of receiving is included herein. The bioreactor component 10 can be divided into a tissue-imaging chamber 12 and a support chamber 14, which are separated by a permeable support structure 16. The permeable support structure 16 is one that allows for fluid communication between the tissue-imaging chamber 12 and the support chamber 14.

In some embodiments, the tissue-imaging chamber 12 of the bioreactor component 10 is configured to be received within a magnetic resonance (MR) imager 50, while, in some embodiments, the entire bioreactor component 10 is configured to be received within a MR imager 50. Even when the entire bioreactor component 10 is to be inserted within a MR imager 50, the tissue imaging chamber 12 is configured to fall within the field-of-view (FOV) of the MR imager 50, while the support chamber 14 is configured to fall outside the FOV of the MR imager 50. As such, the tissue-imaging chamber 12 generally includes at least one fiber optic sensor 18, which is compatible with FOV MR imaging, while the support chamber generally includes the culture media, which, as indicated herein, is in fluid communication with the tissue-imaging chamber 12 via the permeable support structure 16, a heating element 20 to maintain the proper temperature of the culture media, and fluidics 22 to be able to maintain the culture media under suitable conditions.

It would be understood that a heating element 20 in the support chamber 14 needs to be compatible with MR imaging, but, since it falls outside of the FOV, does not need to be compatible with the actual imaging. Therefore, an example of a suitable heating element 20 is a ceramic heater. It would also be understood that fluidics typically refers to at least some form of tubing that is capable of fluidly communicating with one or more components. In a MRI-compatible bioreactor system 1, fluidics 22 associated with the support chamber 14 connect the support chamber 14 with at least one reservoir 24 (e.g., to receive, provide, and/or exchange culture media). In some embodiments, a MRI-compatible bioreactor system 1 can include at least two reservoirs 24; at least one reservoir 24a to contain fresh media and at least one reservoir 24b to receive used or spent media during media exchange. In addition, to facilitate media exchange, a MRI-compatible bioreactor system 1 optionally can include one or more pumps 26.

In some embodiments, the at least one fiber optic sensor 18 in the tissue-imaging chamber 12 is a temperature sensor. Having a temperature sensor in the tissue-imaging chamber 12 allows for the temperature to be monitored, and modified if necessary, during all aspects of cell or tissue growth including, for example, during the actual imaging. In addition or as an alternative to a temperature sensor, the fiber optic sensor 18 in the tissue-imaging chamber 12 can be a $CO_2$ sensor 28 and/or a humidity sensor. In addition, a tissue-imaging chamber 12 of a MRI-compatible bioreactor system 1 can include fluidics 30 for maintaining and/or changing the environment within the bioreactor. For example, fluidics 30 can connect the tissue-imaging chamber 12 with an appropriate source of air 32 (e.g., oxygen ($O_2$) and/or carbon dioxide ($CO_2$)) so as to properly oxygenate the culture.

In some embodiments, the support chamber 14 also includes at least one sensor 34. Since the support chamber is configured to fall outside of the MRI FOV, sensors 34 that are located in the support chamber 14 do not need to be fiber optic. A sensor 34 located in the support chamber 14 can be, for example, a pH sensor and/or a temperature sensor.

Since the bioreactor component of the MRI-compatible bioreactor system is configured to fit inside a MR imager and be imaged continually or at particular intervals, it would be understood by those skilled in the art that the components in the system that communicate and support the bioreactor such as, without limitation, an appropriate source of oxygen, one or more reservoirs, and/or one or more pumps, are exterior to the bioreactor component but remain in fluid communication with the bioreactor component via fluidics whether the bioreactor component is inside or outside the imager.

To sense and change the environment as necessary, a MRI-compatible bioreactor system 1 as described herein also can include one or more microcontrollers 36. The one or more microcontrollers 36 can be in communication, for example, with the one or more fiber optic sensors 18 in the tissue-imaging chamber 12 and/or with the heating element 20 and fluidics 22 in the support chamber 14. In embodiments in which the fiber optic sensor 18 in the tissue-imaging chamber 12 is a temperature sensor, the microcontroller 36 also can be in communication with the heating element 20 in the support chamber 14, such that the temperature of the culture media can be controlled and changed, as necessary or desired. In addition, a microcontroller 36 can be in communication with any additional sensors (e.g., fiber optic or non-fiber optic sensors) used to sense and/or control the environment in the bioreactor component 10. Further, a microcontroller 36 can be used in the process of media exchange (e.g., between the support chamber 14 of a bioreactor component 10 and one or more reservoirs 24 via, for example, one or more pumps 26).

Conventionally, bone constructs are cultured in a $CO_2$ incubator, which provides a suitable environment maintained with respect to temperature, oxygen availability, and relative humidity. The MRI-compatible bioreactor system 1 described herein is not just a replacement for conventional incubators that includes automated media exchange, but the system described herein also offers a unique MR compatibility. The MRI-compatible bioreactor system 1 described herein provides a closely monitored and tightly controlled physiological environment for developing cell or tissue constructs inside an MRI, with continuous non-invasive assessment of the morphogenesis evolution and functional outcome of the cell or tissue constructs through MRI.

In the current design, MRI compatibility was incorporated because it is the most sophisticated, clinically-viable, imaging technique. With proper adjustments, the design can be modified to accommodate other imaging modalities such as Computed Tomography (CT).

An MRI-compatible bioreactor system 1 as described herein can be used to image a biological sample growing in culture. Initially, a biological sample is deposited onto the permeable support structure 16 and appropriate culture conditions are established in the bioreactor 10. Appropriate culture conditions are known to those skilled in the art and typically include a culture media that provides the necessary components to keep alive the cells or tissues (e.g., required minerals, essential nutrients). The culture media also can provide one or more co-factors required by the cells or tissues. Appropriate culture conditions also include maintaining a proper temperature range and pH range.

Appropriate culture conditions require that the culture media be changed periodically. For example, the spent media typically is replaced with fresh media so as to continue to support the growth of the culture. The rate of media exchange is dependent upon the rate of growth of a particular organism or organisms but, under typical culture conditions, media is usually exchanged several times a day (e.g., every 2, 4, 6, 8 or 10 hours), twice a day (e.g., about every 12 hours), at least once a day (e.g., every 18, 20, 22 or 24 hours), or more (e.g., every 30, 40 or 50 hours). In certain instances, the culture media in a bioreactor can be exchanged on a weekly basis or on a monthly basis.

In some embodiments, a feedback system can maintain the $CO_2$ level in the tissue-imaging chamber using two flow controllers to mix $CO_2$ and air based on the value recorded by the $CO_2$ sensor positioned on the output flow from the tissue-imaging chamber. In addition, the quality of the media can be maintained by media exchange once every 6 hours, during which time, a pH sensor can determine the pH of the bioreactor. Further, a humidity sensor also can be included in a MRI-compatible bioreactor system as described herein to maintain the proper humidity in the bioreactor.

At any time after initiating the culture, at least the tissue imaging chamber of the bioreactor component can be inserted into a MR imager and imaged. As discussed herein, the bioreactor component is inserted into the MR imager such that the tissue imaging chamber falls within the field-of-view (FOV) of the MR imager and the support chamber falls outside the FOV of the MR imager. The biological sample can be imaged continuously for a period of time (e.g., several milliseconds, one or more seconds, one or more minutes, or longer) or at particular intervals (e.g., once every second, once every minute, multiple times per minute, several times per hour, or once or multiple times a week). It would be appreciated that the MRI-compatible bioreactor can be removed from the MR imager in between imaging, or it can remain inside the imager even when images are not being obtained.

A biological sample contained within the MRI-compatible bioreactor system described herein can be imaged once or multiple times without compromising the sample. That is, none of the biological sample needs to be removed from the bioreactor prior to or during imaging, and the components required for maintaining the viability of the culture are designed such that they do not interfere with the imaging process. Thus, the bioreactor remains a "closed" system, even when introduced (and re-introduced) into an imager for imaging.

As used herein, the biological sample refers to any cell sample or any tissue sample. Representative cells include, without limitation, osteoblasts, osteoclasts, osteocytes, chondrocytes, hepatocytes, islet cells, myocytes, epithelial cells, kidney cells, and neurons, while representative tissues include, without limitation, bone, cartilage, liver, pancreas, muscle, epithelium, kidney, brain, uterus, ovarian, and testes.

Simply by way of example, bone tissue engineering is emerging as a promising alternative for creating functional substitutes for bone repair and replacement. Both autologous and allogeneic bone grafts are used clinically as bone substitutes; however, the availability of compatible grafts is limited because harvesting bone is painful and the procedure carries significant infection risks. Therefore, the MRI-compatible bioreactor described herein can be used to produce bone tissue. In addition, as tissue engineering grows in complexity to match the geometry and function of a patient's unique needs, it becomes increasingly important to non-invasively follow the spatial and temporal pattern of growth and maturation of the bone tissue in vitro. The MRI-compatible bioreactor system described herein is expected to help produce tissue engineered bone constructs with proper osteogenic phenotype expression, which can expedite the clinical translation of bone tissue engineered products and improve the success rate of bone transplantation.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Design and Configuration of a Prototype e-Incubator

A basic prototype of a MRI-compatible bioreactor has been developed. Shown in FIG. 1, a cylindrical chamber system with an outer diameter of 3 cm was designed. Made of polycarbonate and manufactured by 3D printing, the system included a support chamber and a tissue imaging (TI) chamber. Tissue samples were positioned atop a permeable support inside a tissue holder within the TI chamber. There were many challenges associated with MRI compatibility when implementing the design. For example, in order to truthfully represent the sample's environmental condition, one design specification requires measuring and adjusting the temperature of the sample's direct surroundings with minimal MR susceptibility artifacts. Since the TI chamber is inside the MRI and, therefore, is encompassed by the MRI field-of-view (FOV), while the support chamber is outside the MRI and the MRI FOV, the solution used was to place a fiber optic temperature probe (SA Instruments, Inc. Stony Brook, N.Y.) adjacent to the sample in the TI chamber (inside FOV) while regulating the temperature by an MR compatible ceramic heater located in the support chamber (outside FOV).

For regulating all environmental conditions inside the TI chamber for biological samples, a Microchip PIC® MCU was used to operate a closed-loop feedback system via a C program. By integrating both hardware and software, MCUs are embedded as "brains" in almost all "SMART" devices, from consumer electronics to automobiles to medical systems. Physiological conditions inside the TI chamber were detected by physical and biochemical sensors and sent to the MCU. The MCU compared the received sensor signals with pre-determined thresholds and sent control signals to other mechatronics to guide their actions for adjusting those conditions. For example, the MCU acquired data from the temperature, $CO_2$, humidity sensors at a rate of one per ten seconds and the pH was evaluated during every media exchange. A peristaltic pump was used to exchange media based on the measured pH level; two flow controllers were used to mix air and $CO_2$ to create proper concentration of $CO_2$ for the engineered tissues in the chamber.

A preliminary study on human mesenchymal stem cells (hMSCs) derived osteogenic construct was performed using the MRI-compatible bioreactor prototype. For constructs preparation, human bone MSCs were isolated from fresh marrow cells provided commercially (Lonza, Walkersville, Md.). Upon 80% confluence, the hMSCs were trypsinized, counted, and passaged at a density $5 \times 10^3$ cells/$cm^2$ and expanded in vitro. Expanded to passage 4-5, MSCs were re-suspended and seeded into gelatin sponges (Pharmacia & Upjohn, Kalamazoo, Mich.). Osteogenic medium (Xu et al., 2006, *Phys. Med. Biol.*, 51:719-32) was used to induce osteogenesis in the construct. FIG. 2 presents the data from this study. The viability and growth of the construct was validated with MRI results: lower signal intensity in construct at Week-2 compared to Week-1, suggesting increased mineralization and development of bone-like tissue [FIG. 2(*c*) vs. FIG. 2(*b*)]. FIG. 2(*d*) shows automatic adjustments of the temperature (between 36 to 37° C.) and $CO_2$ level (5%) in the construct's surroundings.

As described herein, the MRI-compatible bioreactor prototype was integrated with a high resolution MRI scanner and TE bone constructs were successfully cultured for two weeks. The following Examples demonstrate that such a bioreactor can provide accurate controls to maintain the proper physiological environment that is comparable to a conventional $CO_2$ incubator. In addition, the following Examples demonstrate that such a bioreactor truly is MRI compatible and enables prolonged growth (e.g., bone construct growth) to be continuously and non-invasively monitored.

Example 2

Verifying the Accuracy of the Operation of the MRI-Compatible Bioreactor

Verifying that such a bioreactor can precisely control the internal environmental growth conditions for developing tissue is required before placing a TE culture inside an MRI scanner.

In order to create a reliable environment comparable to a conventional incubator, targeted operating parameters for the bioreactor are 37° C., 5% $CO_2$ level, and 95% relative humidity. Regular media exchange is performed for maintaining proper pH level. Prior to loading biological samples into the bioreactor, all components are dissembled. All relevant components inside the TI chamber are cleaned with Alcon, soaked in 1M NaOH for an hour, and then rinsed twice with sterile water, to eliminate possible contamination.

Two types of biological samples were tested:
Standard culture media as a phantom for verifying the accuracy of adjusting physiological conditions and examining possible contamination inside the bioreactor. The phantom is tested in the bioreactor for one week, during which time, the temperature, $CO_2$, and humidity conditions are recorded at a rate of one per ten seconds and the pH evaluated for every media exchange (scheduled once every 6 hours). The starting and ending times of each media exchange are recorded. Used media is examined under an inverted microscope for contamination. This experiment is repeated twice, and, before starting the second set of experiments, the bioreactor is dissembled, cleaned, reset, and filled with fresh standard culture media.

TE bone constructs for confirming that the e-incubator provides a suitable environment for engineered tissues. A TE osteogenic construct of size 4 mm×4 mm×4 mm is prepared as described in Example 1 and placed inside the TI chamber for four weeks atop the permeable support. In addition to recording physiological conditions as descried above, following four weeks of constructs culture in the bioreactor, constructs are fixed with 10% neutral buffered formalin and sectioned. This experiment is repeated twice as well. In order to confirm the viability of the TE bone constructs, at the end of each experiment, sections are stained with hematoxylin and eosin (H&E) and von Kossa to examine mineralization and calcium deposition. In parallel to the experiments conducted in the bioreactor, three TE bone constructs are cultured in a conventional incubator. After four weeks of culture, all samples in the conventional incubator are fixed and undergo similar histological analysis.

All data collected from above experiments, i.e., three sets of one-week phantom data and three sets of four-week TE construct data, are analyzed statistically to testify the accuracy of bioreactor operation:

For each media exchange, the mean time duration required for temperature, $CO_2$, and humidity to return to normal operating mode are computed based on the average difference of the end and starting times. For all the raw data, data points recorded during media exchange are filtered and the rest of the data represents normal operating mode of the bioreactor. For each physiological parameter in each individual set of experiment, e.g., temperature, $CO_2$ level, or humidity, the mean and standard deviation of measurements during the normal operating mode are computed.

The following criteria are used to determine if the bioreactor performance is adequate.

All of the physiological parameters should return to the normal operating mode within 5 minutes, which is determined based on the time it takes for a tissue engineer to exchange the media. The bioreactor is considered satisfactory if the confidence level is at least 95% that, every time, the duration is less than 5 minutes.

The bioreactor is considered accurate if the confidence level is at least 95% that every temperature measurement is within 1% of 37° C., and every $CO_2$/humidity measurement is within 5% of its respective target.

For each individual parameter, the means and standard deviations of one-week phantom are compared to those of four-week TE constructs to determine if there is significant difference with respect to the biological sample and the length of time it is cultured in the bioreactor.

Histological review of TE constructs cultured both in the bioreactor and the conventional incubator are performed in a blinded study by a Board-certified pathologist for assessing possible variation in construct development between a conventional incubator and the bioreactor.

All physiological conditions of the tissue sample's surroundings are closely monitored and properly regulated autonomously via a closed-loop system. Preliminary studies indicate that the bioreactor performs better than or at least comparable to conventional incubators, likely due to reduced human handling (i.e., transferring the samples in a biosafety cabinet to perform media exchange is no longer needed).

Example 3

Validating the Ability of the e-Incubator in Culturing Bone Constructs Using Quantitative MRI Using engineered bone, an MRI-compatible bioreactor facilitates non-invasive high-resolution imaging for the continuous evaluation of the constructs concurrent with in vitro tissue development.

In order to confirm that the bioreactor mechatronics inside the magnet are MRI-compatible and do not affect MRI sensitivity in detecting bone formation, engineered bone constructs were used. In order to take advantage of the bioreactor's capability of culturing tissue samples non-interruptedly, the tissue holder of the bioreactor is revised to include fine grids so that five samples can be cultured and assessed simultaneously. Constructs cultured in a conventional incubator are labeled "incubator" group and constructs in the bioreactor are labeled "e-incubator" group.

Thirty TE bone constructs of size 3 mm×3 mm×3 mm are prepared with the procedures described in Example 1. On Day 0, constructs are divided into two groups: twenty five "incubator" bone constructs and five "e-incubator" bone constructs. All five "e-incubator" bone constructs are loaded in the tissue holder of the bioreactor and then the 3 cm cylindrical chamber system is inserted into a 4 cm Millipede radiofrequency (RF) imaging probe of a 9.4 T (400 MHz for protons) 89 mm vertical bore MRI scanner (Agilent, Santa Clara, Calif.), equipped with 100 G/cm maximum triple axis gradients. The entire construct is divided as six axial slices with a thickness of 500 μm and a spatial resolution of 100 μm×100 μm. For MRI acquisitions, MR spin-spin relaxation time ($T_2$) is measured by applying a spin echo imaging sequence to acquire 32 echoes with 4 seconds of repetition time (TR) and 8 milliseconds echo spacing (TE). These measurements are acquired on a daily basis. For the twenty five "incubator" bone constructs, TE samples are allocated into a test tube and subjected to MRI. Since it is not possible to perform daily MRI with a conventional incubator; measurements are acquired only at five discrete time points, i.e., Day 0, 7, 14, 21, and 28, with five samples at each specific time point. At the end of tissue culture, i.e., Day 28, five remaining "incubator" samples and all five "e-incubator" samples are fixed and subjected to histological analysis. These experiments are repeated on control constructs prepared only with basic culture media. Because the controls are not expected to develop, no matter in a conventional or the bioreactor, MRI only is acquired at specified time points for both "incubator" and "e-incubator" groups.

The effectiveness of the bioreactor on growing osteogenic constructs inside a MRI scanner is quantified by statistical analysis. For quantitative MRI analysis, the $T_2$ relaxation time is analyzed using a mono-exponential model and mapped for the entire construct using a custom developed MATLAB program. Based on preliminary results, the mean value of the $T_2$ in bone constructs is expected to exhibit a greater than 50% reduction after 4 weeks in culture, while the control constructs show no significant difference in $T_2$ with time (Xu et al., 2006, *Phys. Med. Biol.*, 51:719-32). The bioreactor is validated when statistical tests on $T_2$ reject the hypotheses that (i) the mean value of "e-incubator" bone constructs is greater than or equal to that of "incubator" bone, (ii) the variance of "e-incubator" bone constructs is greater than or equal to that of "incubator" bone, and (iii) the mean value of "e-incubator" control constructs is different than that of "incubator" control. Histological analysis is used as a reference to confirm bone formation in TE bone constructs.

The use of a detailed imaging assessment technique provided by MRI-integrated bioreactor will allow the production of high quality TE constructs, to thereby improve the success rate of bone replacement implantation. In some instances, the bioreactor would only be placed inside the magnetic field during MRI sessions, since the effect of a strong magnetic field on engineered tissues' growth is not well understood. Also, recent advances such as zero echo time MRI may be useful, for example, to study late growth stages of osteogenesis, since intensive mineralization may hamper conventional MRI.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. An MRI-compatible bioreactor system, comprising:
   a bioreactor comprising a tissue-imaging chamber and a support chamber that are separated by a permeable support that allows for fluid communication between the chambers, wherein at least the tissue-imaging chamber of the bioreactor component is configured to be received within a magnetic resonance (MR) imager;
   wherein the tissue-imaging chamber comprises at least one fiber optic sensor and fluidics capable of fluidly communicating with a source of oxygen, wherein the tissue imaging chamber is configured to fall within the field-of-view (FOV) of the MR imager; and
   wherein the support chamber comprises a heating element and fluidics capable of fluidly communicating with at least one reservoir, wherein the support chamber is configured to comprise culture media and maintain the culture media under suitable conditions, wherein the support chamber is configured to fall outside of the FOV of the MR imager.

2. The bioreactor system of claim 1, wherein the at least one fiber optic sensor is a temperature sensor.

3. The bioreactor system of claim 1, further comprising a microcontroller in communication with the at least one fiber optic sensor.

4. The bioreactor system of claim 1, further comprising a microcontroller in communication with the heater.

5. The bioreactor system of claim 1, further comprising a microcontroller in communication with the at least one fiber optic sensor and the heater, wherein the at least one fiber optic sensor is a temperature sensor.

6. The bioreactor system of claim 1, wherein the support chamber further comprises at least one non-fiber optic sensor.

7. The bioreactor system of claim 6, wherein the at least one non-fiber optic sensor is selected from the group consisting of a temperature sensor and a pH sensor.

8. The bioreactor system of claim 6, wherein the at least one non-fiber optic sensor is in communication with a microcontroller.

9. The bioreactor system of claim 1, further comprising a pump configured to promote fluid communication between the at least one reservoir and culture media in the support chamber.

10. A method of imaging a biological sample, comprising:
    providing the MRI-compatible bioreactor system of claim 1, wherein the tissue imaging chamber comprises a biological sample and the support chamber comprises culture media;
    inserting at least the tissue imaging chamber of the bioreactor component into a MR imager such that the tissue imaging chamber falls within the field-of-view (FOV) of the MR imager and the support chamber does not fall within the FOV of the MR imager; and
    imaging the biological sample using the MR imager.

11. The method of claim 10, wherein the biological sample is a tissue sample or a cell sample.

12. The method of claim 10, further comprising repeating the inserting and imaging steps at least twice.

13. The method of claim 12, wherein repeating the inserting and the imaging steps at least twice does not require removing the biological sample or any portion thereof from the bioreactor.

14. The method of claim 12, wherein repeating the inserting and the imaging steps at least twice does not compromise the biological sample or the culture media.

15. The method of claim 10, further comprising repeating the imaging step at least twice, wherein the inserting step is performed only once.

16. The method of claim 10, further comprising exchanging the media in the support chamber with fresh media in the at least one reservoir via the fluidics.

17. The method of claim 16, further comprising repeating the exchanging step at least twice separated by a period of time.

18. The method of claim 17, wherein the period of time is selected from the group consisting of hours, days, weeks, and months.

* * * * *